(12) United States Patent
Glocker

(10) Patent No.: US 8,152,772 B2
(45) Date of Patent: Apr. 10, 2012

(54) ATTACHMENT FOR A SYRINGE OR A CARTRIDGE

(75) Inventor: Joachim Glocker, Weingarten (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 346 days.

(21) Appl. No.: 12/516,332

(22) PCT Filed: Dec. 12, 2007

(86) PCT No.: PCT/EP2007/010844
§ 371 (c)(1), (2), (4) Date: May 26, 2009

(87) PCT Pub. No.: WO2008/071403
PCT Pub. Date: Jun. 19, 2008

(65) Prior Publication Data
US 2010/0030160 A1    Feb. 4, 2010

(30) Foreign Application Priority Data
Dec. 13, 2006 (DE) .......................... 10 2006 058 719

(51) Int. Cl.
*A61M 5/178* (2006.01)
*A61M 5/315* (2006.01)
*B65D 47/00* (2006.01)
(52) U.S. Cl. .................... 604/167.03; 604/236; 222/544

(58) Field of Classification Search .................... 604/33, 604/34, 167.03, 167.04, 236, 237, 247, 249, 604/250; 222/211, 522, 520, 521, 525, 526, 222/531, 532, 537, 544, 545, 546, 548, 549, 222/552, 553, 559, 562, 563
See application file for complete search history.

(56) References Cited

U.S. PATENT DOCUMENTS

| | | | |
|---|---|---|---|
| 3,401,845 A * | 9/1968 | Bach | 222/211 |
| 3,989,045 A | 11/1976 | Van Eck | |
| 4,130,117 A | 12/1978 | Van Eck | |
| 4,243,034 A * | 1/1981 | Brandt | 604/167.01 |
| 4,342,184 A | 8/1982 | Van Eck et al. | |
| 4,425,122 A * | 1/1984 | Cohen | 604/237 |
| 4,781,702 A * | 11/1988 | Herrli | 604/244 |
| 4,919,167 A * | 4/1990 | Manska | 137/512 |
| 5,064,416 A * | 11/1991 | Newgard et al. | 604/167.03 |
| 5,269,771 A * | 12/1993 | Thomas et al. | 604/539 |
| 5,458,640 A * | 10/1995 | Gerrone | 604/264 |
| 5,489,274 A | 2/1996 | Chu et al. | |
| 6,050,978 A * | 4/2000 | Orr et al. | 604/249 |
| 6,626,418 B2 * | 9/2003 | Kiehne | 251/149.6 |

(Continued)

FOREIGN PATENT DOCUMENTS
DE            110177 A       4/1900
(Continued)

*Primary Examiner* — Jackie Ho
*Assistant Examiner* — William Carpenter
(74) *Attorney, Agent, or Firm* — Harness, Dickey & Pierce, P.L.C.

(57) ABSTRACT

The invention relates to an attachment or a cartridge comprising a sealing element having an opening for a medium located in the syringe or cartridge or to be introduced into the syringe or cartridge. The attachment is characterized by an actuating device which, in a first functional position, exerts a force on the wall of the opening in such a way that the opening is closed, and leaves the opening open in a second functional position.

16 Claims, 2 Drawing Sheets

U.S. PATENT DOCUMENTS

| | | |
|---|---|---|
| 7,008,404 B2 * | 3/2006 | Nakajima ............... 604/158 |
| 8,006,853 B2 * | 8/2011 | Delage .................. 215/237 |
| 2002/0062106 A1 * | 5/2002 | Chu et al. ............. 604/167.01 |
| 2005/0177100 A1 | 8/2005 | Harper et al. |
| 2005/0215952 A1 * | 9/2005 | Brunel et al. ............ 604/111 |

FOREIGN PATENT DOCUMENTS

| | | |
|---|---|---|
| DE | 2415496 A1 | 10/1975 |
| DE | 2650951 A1 | 5/1978 |
| DE | 69533453 T2 | 9/2005 |
| EP | 0901389 B1 | 9/2004 |
| WO | 2005/039669 A | 5/2005 |

* cited by examiner

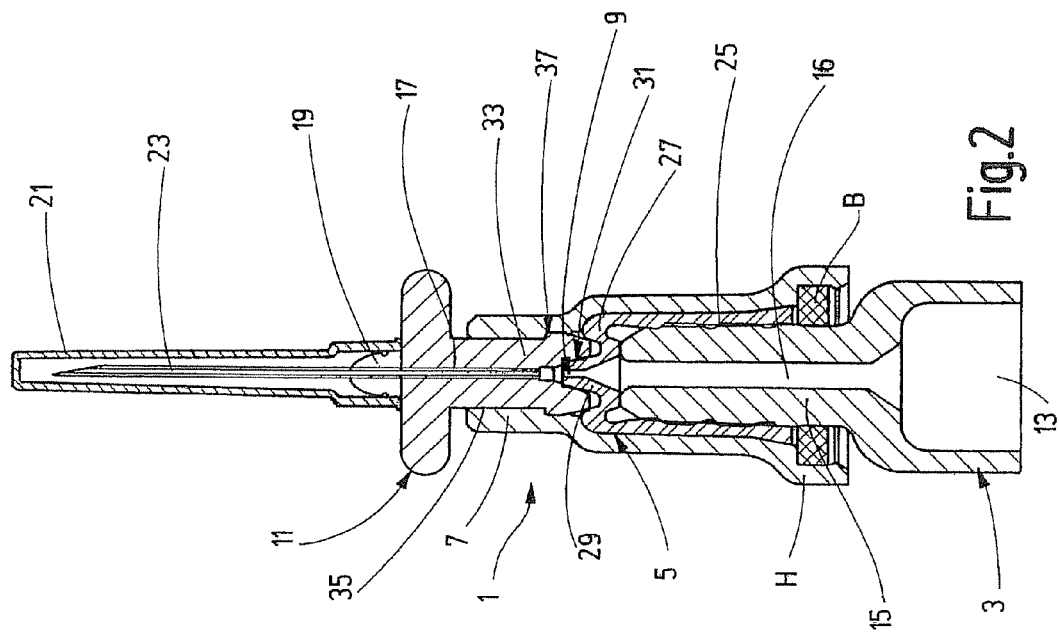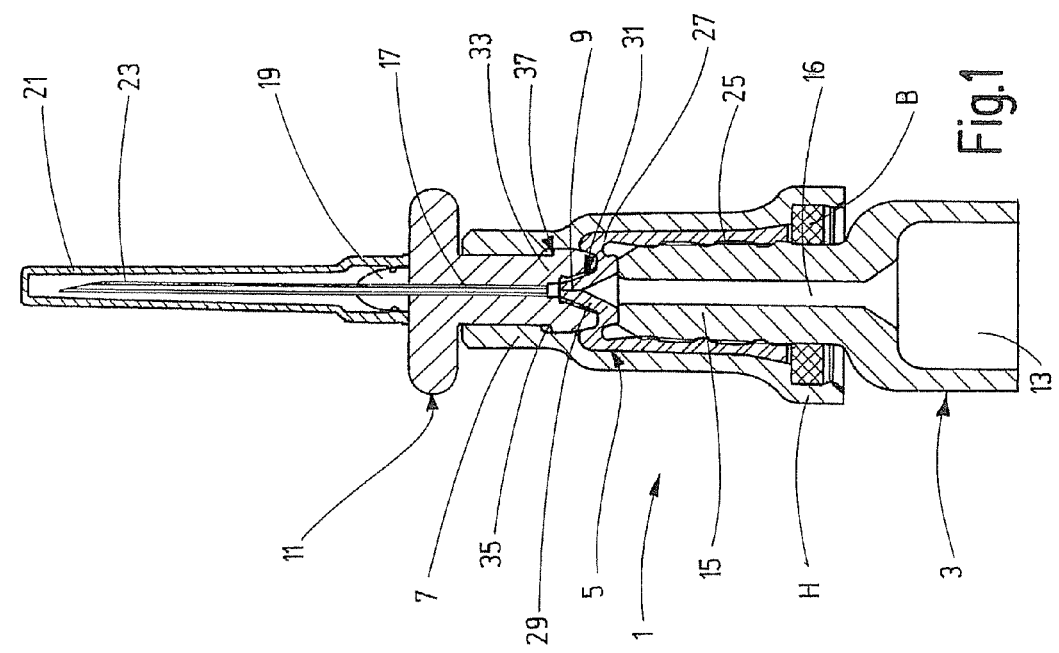

ATTACHMENT FOR A SYRINGE OR A CARTRIDGE

CROSS-REFERENCE TO RELATED APPLICATIONS

This application is a 371 U.S. National Stage of International Application No. PCT/EP2007/010844, filed Dec. 12, 2007. This application claims priority to German Patent Application No. DE 10 2006 058 719.7, filed Dec. 13, 2006, which application is expressly incorporated herein by reference.

FIELD

The invention relates to an attachment for a syringe or a cartridge with a sealing element.

BACKGROUND

Attachments of the kind discussed herein are known. They are suitable for tightly sealing the interior of the syringe or cartridge and to protect against impurities. It is known to use a piercing membrane for sealing syringes or cartridges among others in connection with an attachment of the kind discussed herein. It has been shown, that particles can be released when the membrane is pierced that can enter the interior of the syringe or cartridge and are then possibly administered with the content of the syringe/cartridge to a patient.

SUMMARY

Therefore, the object of the invention is to provide an attachment that omits said disadvantage.

In order to solve said object, an attachment is proposed. It comprises a sealing element with an opening, via which a liquid can be introduced into or removed from the syringe or cartridge. The attachment is characterized by an actuating device that interacts with the sealing element and which closes or releases the opening therein. This is achieved by the actuating device exerting a force on the wall of the opening in a first functional position in such a way that the opening is closed. In a second functional position, no force or at least only a minor force is exerted on the wall, so that the opening is open. Thus, the sealing element is designed in such a way that piercing of the material of the sealing element is not necessary for creating an opening to the interior of the syringe or cartridge. In fact, an opening is closed or left open by means of an actuating device. Thus, it is impossible that any particles are detached from the sealing element that can reach into the interior of the syringe or cartridge and thus can reach into a patient with an injection liquid.

A particularly preferred embodiment of the attachment is where the actuating device and the sealing element are designed in a way such that opening and closing the opening can be repeated.

Further designs result from the remaining sub claims.

DRAWINGS

The invention is further explained by means of the drawings in the following, wherein:

FIG. 1 shows a longitudinal section through a first embodiment of an attachment with a closed opening;

FIG. 2 shows a longitudinal section through the embodiment according to FIG. 1 with an opened opening;

DETAILED DESCRIPTION

Figure 3:
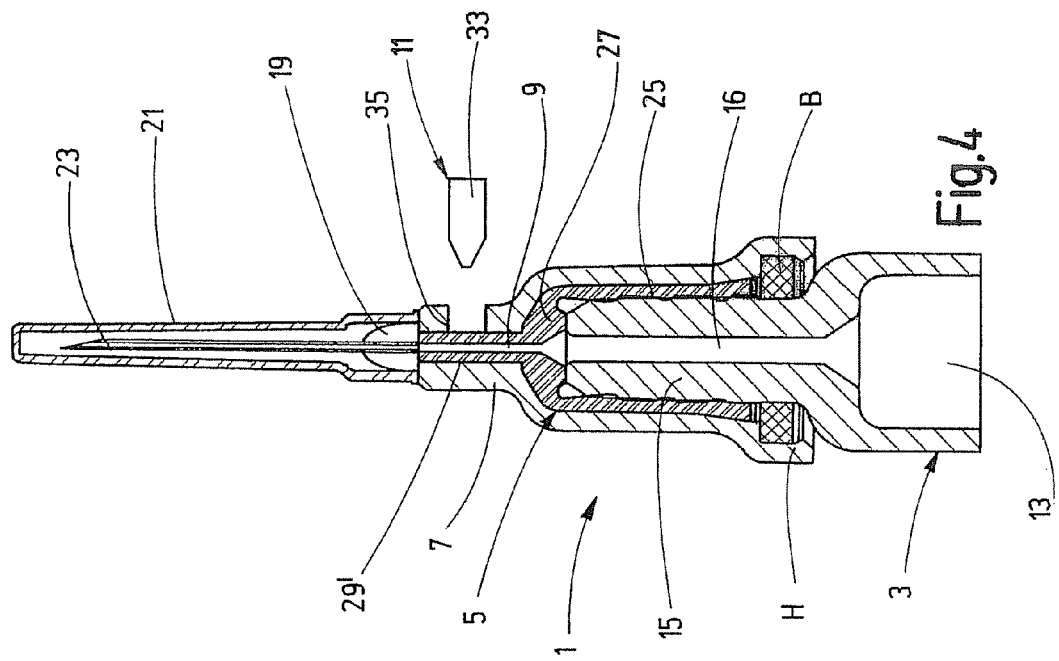
FIG. 3 shows a longitudinal section through a second embodiment of an attachment with a closed opening and FIG. 4 shows a longitudinal section through the embodiment according to FIG. 3 with an opened opening.

FIG. 1 shows an attachment 1 for a syringe 3 with a sealing element 5, housed inside the base body 7 of the attachment 1, being designed in a hollow way and comprising an opening or outlet 9. The attachment 1 comprises an actuating device 11, interacting with the sealing element 5 and being in a first functional position in which the opening 9 in the sealing element 5 is closed. The interior 13 of the syringe 3 is thus tightly sealed.

The embodiment of the syringe 3 shown here comprises a protrusion 15, onto which the attachment 1 is fastened. The protrusion 15 is hollow inside, so that the interior 13 of the syringe 3 has a fluid connection with the opening 9 in the sealing element 5 via an inlet 16. Because of the opening 9 being closed, the interior 13 is hermetically sealed and is protected against impurities. The sealing element 5 is preferably made of a thermoplastic elastomer (TPE), providing a high degree of safety against microbiological impurities.

The actuating device 11 comprises a passage channel 17 that is aligned with the opening 9. As an example, a projection 19 is provided here on the upper side of the actuating device 11 facing away from the syringe 3, having a cap 21 for a cannula 23 that is at least regionally inserted, preferably glued, into the passage channel 17 of the actuating element 11. It is also possible to mold the cannula 23 into the base body of the actuating device 11 or to fasten it by means of a plastic injection molding process. It should be specifically stated here, that the attachment 1 can be provided with any medical connection and that the cannula 23 and the cap 21 are only indicated as an example.

With the embodiment described here, the base body 7 of the attachment 1 is designed as a sleeve. It only surrounds the protrusion 15 and not the syringe 3. It should be also pointed out, that the connection of the attachment 1 on the syringe 3 can be freely chosen. It is important, that the sealing element 5 can seal the interior 13 of the syringe. Therefore, the attachment 1 is designed in a cap shape and houses a sealing element 5 that is preferably designed in a cap shape. This can be inserted or injected into the base body 7 of the attachment 1. It comprises a slightly conical region 25 and a sealing region 27 that can close the access 16 to the interior 13 of the syringe 3. The outlet 9 is provided in said sealing region 27, that is to say in the embodiment according to FIG. 1, in a conical section 29 that extends upward in the direction of the actuating device 11 as cone and thus comprises a cone sleeve shaped outer wall.

The actuating device 11 acts on the conical section 29 of the sealing element 5 in such a way that a force is exerted from the outside on said section, so that the wall of the outlet 9 is displaced to the inside and the outlet 9 is thus closed. Therefore, the actuating device 11 comprises an actuating region 31 that is formed here by a conical widening of the passage channel 17. The inner contour of the conical widening is adapted to the outer contour of the conical section 29 in such a way that the widening lies flat against the conical section 29 and thus forces the material of the sealing element 5 towards the inside and closes the opening 9. The actuating region 31 can also be formed by a cylindrical region being provided with a step that presses from the outside on the conical section 29 and thus closing the opening 9.

The actuating device 11 comprises a displaceable actuating element 33 in relation to the base body 7 of the attachment that is arranged coaxially to the opening 9 in the direction of a perceived middle axis of the opening 9 relative to the base body 7 of the attachment 1 and comprising the actuating region 31.

FIG. 1 shows the actuating device 11 in a first functional position. In this position, the actuating element 33 is displaced towards the bottom, that is to say in the direction of the sealing element 5, so that the conical widening of the passage channel 17, that is to say the actuating region 31, exerts a pressure force on the conical section 29 of the sealing region 27 from the outside and closes the opening 9. The actuating element 33 is for example designed in a cylindrical way and extends through a recess 35 into the base body 7. The actuating element 33, as well as the recess 35 have a preferred cylindrical design.

A locking device 37 is provided here, that holds the actuating device 11 in the position depicted in FIG. 1 in a closed manner. The term closed manner, stands here for the actuating element 33 not being able, particularly not accidentally, to be moved from a first functional position as depicted in FIG. 1, so that the opening 9 is securely closed. On the outside of the actuating element 33 at least one notch is provided for example, engaging in a recess or groove in the inner surface of the recess 35, so that the actuating element 33 is securely held in the first functional position.

FIG. 2 shows the embodiment of the attachment 1 depicted in FIG. 1 in a second functional position. Same parts are provided with the same reference numbers, so that no description thereof is necessary.

The actuating element 33 was displaced against the force of the closing device 37 into a second functional position, wherein it is preferably held again in a closed manner. The actuating device 11, particularly the actuating element 33 thereof, was displaced in the direction of the middle axis of the opening 9 towards the top, so that the inner wall of the conical widening of the passage channel 17 lies at a distance to the outer surface of the conical section 29 of the sealing region 27 of the sealing element 5. Thus, the opening 9 can open, as shown in FIG. 2.

The second functional position of the actuating device 11 or of the actuating element 33 is chosen in such a way that the force acting from the conical widening on the conical section 29 from the outside is so low that the opening 9 can open. Thus, it is not absolutely necessary for the inner wall of the conical widening to be arranged at a distance to the outer surface of the conical section 29.

The material of the sealing element 5 is chosen in a way such that the opening 9 springs towards the outside due to the inherent elasticity of the conical section 29 when the inner wall of the conical widening of the passage channel 17 exerts no or only a small force on the conical section 29.

Due to the inherent elasticity of the sealing element 5, the conical section 29 can be forced several times into its closed position by the actuating element 33, as shown in FIG. 1. Every time the actuating device 11 is displaced into the second functional position according to FIG. 2, that is to say when the actuating element 33 is displaced to the top, the conical section 29 of the sealing region 27 can widen and release the opening 9. Thus, the attachment 1 can be easily reclosed and no membrane has to be pierced when opening an access to the interior 13 of the syringe 3 from which particles could be removed and could endanger a patient.

FIG. 3 shows a longitudinal section through a second embodiment of an attachment 1 with a closed opening 9. Parts that are identical or that are functionally equal to the ones from FIGS. 1 and 2 are provided with the same reference numbers.

FIG. 3 shows an attachment 1 that is attached on a syringe 3 and comprises a sealing element 5. As an example, the attachment 1 is again attached to a protrusion 15 with an access 16 that leads to the interior 13 of the syringe 3 and aligns with an opening 9 in the sealing element 5. Said sealing element surrounds the protrusion 15 with a cylindrical region 25 and comprises a sealing region 27.

With the embodiment shown here, the sealing region 27 comprises a cylindrical section 29', into which the opening 9 also extends and which is also aligned with the access 16.

It is also shown here, that the sealing element 5 can preferably also be designed as sealing disc, from which the cylindrical section 29' would then originate.

On the upper end of the base body 7 of the attachment 1 facing away from the syringe 3, a protrusion 19 for a cap 21 is provided which surrounds a cannula 23. It has to be mentioned here, that the cannula is only shown as an example. Any medical connection can be provided here.

An actuating device 11 is also provided here, comprising an actuating element 33, acting on the opening 9. Here however, the actuating element 33 can not be displaced in the direction of the middle axis of the opening 9, as shown in FIGS. 1 and 2, but acts laterally on the cylindrical section 29' and thus exerts a force on the wall of the opening 9, so that the opening is closed in a first functional position of the actuating element 33, as shown in FIG. 3.

The actuating device 11 acts on the cylindrical section 29' of the sealing region 27 of the sealing element 5 due to a recess 35 in the base body 7 of the attachment 1.

Figure 4:
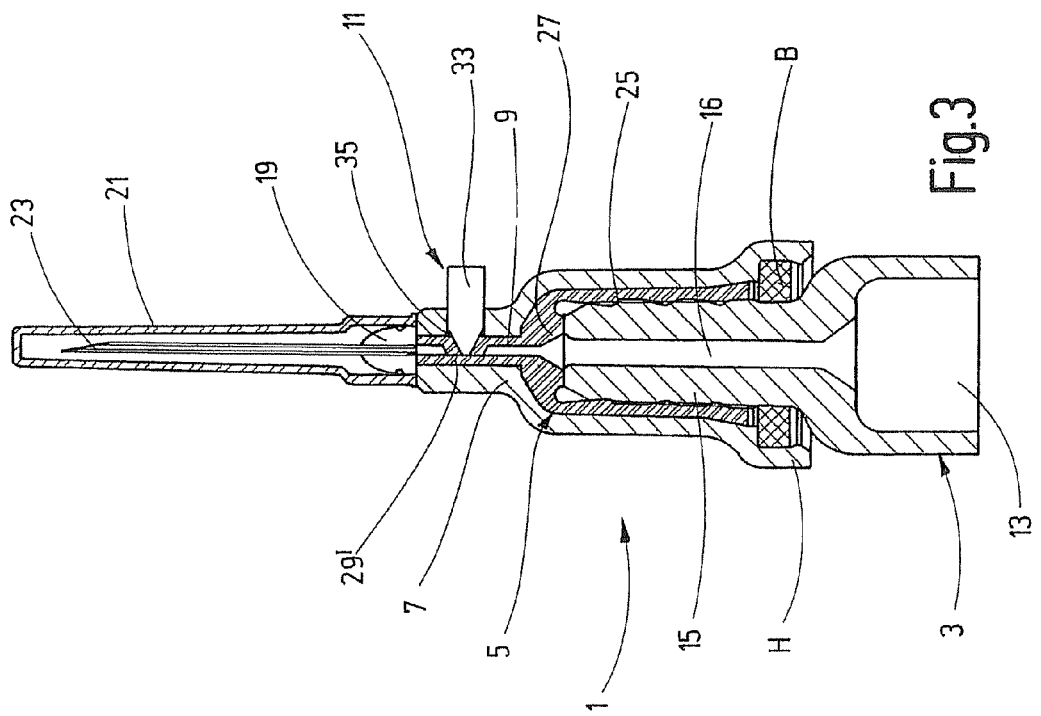

FIG. 4 shows the embodiment of the attachment 1 depicted in FIG. 3, wherein the actuating device 11 is arranged in the second functional position, in which the actuating element 33 does not exert a force on the cylindrical section 29' from the outside, but is arranged at a distance thereto. The actuating element 33 could also rest against the outer side of the cylindrical section 29'. It is important, that the force exerted by the actuating element 33 is so low, that the wall of the opening 9 is not indented, as shown in FIG. 3.

Due to the inherent elasticity of the sealing element 5, which is preferably also made of TPE, the opening 9 is closed under force action by the actuating element 33, that is to say it can be effectively squeezed off. With a lower force of the actuating element 33 or when lifting the actuating element 33 from the cylindrical section 29' however, the opening 9 is opened again. The opening 9 can thus be opened and closed several times, without it being necessary to pierce a membrane in order to reach the interior 13 of the syringe 3. This ensures that no particles are dislodged from a membrane, which could lead to endangering a patient.

The conically pointed end of the actuating element 33 at the side facing the cylindrical section 29' can also be designed in a more or less blunt way. The force acting on the cylindrical section 29' that compresses the wall of the opening 9 and leads to a closure is important. One or a plurality of actuating elements acting on the cylindrical section 29' can be provided, that are arranged in the longitudinal direction of the opening 9 in a displaced way or in a perceived plane, whereon the opening 9 is aligned perpendicular, opposite from or in a star shape to the cylindrical section 29'.

The actuating device 11 can comprise a pivotable actuating element 33 that is pivoted through the recess 35 against the cylindrical section 29' in a lateral way. It is also perceivable, to insert a screw into the wall of the base body 7 of the attachment 1, which is screwed more or less far into the direction of the cylindrical section 29' and causes the opening 9 to stay closed or open.

Furthermore, it is also perceivable to press the actuating element 33 through a sleeve that can be displaced in the direction of the opening 9 with a more or less strong force towards the inside against the cylindrical section 29', for example through a sliding or threading sleeve, in order to close the opening 9 in a first functional position and to release the opening 9 in a second functional position.

Generally this applies also for the embodiment according to FIGS. 1 and 2: The actuating element 33 described therein is axial due to tensile and pressure forces, that is to say, displaceable in the direction of the opening 9. It is possible, to design the actuating element 33 as a screw with an actuating region 31 that is screwed more or less far into the recess 35 and thus acts on the conical section 29 with a more or less strong force and thus closes the opening 9 or releases the opening 9.

The explanations convey that the attachment 1 can also be directly put on the base body 7 of the syringe 3, so that the protrusion 15 may be omitted. The design of the sealing element 5 with the conical section 29 or with the cylindrical section 29' is important. In this case, the sealing element 5 may also be designed as a disc.

In FIGS. 1 to 4, a retaining ring H was provided on the end of the attachment 1 facing the syringe 3 as an example, that is connected to the base body 7 of the attachment 1 via a predetermined braking line and which is put on a fastening ring B in a closing manner, that is attached on the syringe 3 or the cartridge, in this case at the protrusion 15. This embodiment may also be omitted.

Finally it should be mentioned here, that the attachment 1 can not only be used with a syringe 3, but also with a cartridge.

Both examples of embodiments of the attachment 1 according to FIGS. 1 and 2 or according to FIGS. 3 and 4 have in common, that the opening 9 in the sealing element 5 that creates a connection to the interior 13 of the syringe 3, can be opened and closed several times.

Thus it is possible to administer the content of a syringe 3 in a plurality of individual doses to one or several patients. The syringe 3 can be easily closed between each application in a simple manner, for example also for exchanging the cannula 23.

It is also possible to fill the syringe 3 with a medium and to add it to a freeze drying process with the opening 9 being opened. The obtained lyophilisate can then be securely enclosed in a syringe or cartridge by closing the opening 9.

It is for example also possible to apply a vacuum to the interior 13 of the syringe 3, to introduce the cannula 23 into a vein of a patient and to then open the opening 9 in order to take blood due to the vacuum in the syringe. Thereafter, the syringe can be closed in a simple manner by means of the actuating device 11, that is to say, the opening 9 is sealed off by means of the actuating element 33.

The invention claimed is:

1. An attachment for a syringe or a cartridge comprising:
   a sealing element having an opening for a medium located in the syringe or cartridge or to be introduced into the syringe or cartridge; and
   an actuating device for exerting a force on a wall of the opening in a first functional position such that the opening is closed, and leaves the opening open in a second functional position;
   wherein the sealing element includes a conical section through which the opening extends and the actuating device includes a passage channel with an actuating region acting on the conical section, the actuating region being formed by a conical widening of an interior diameter of the passage channel, and the passage channel being aligned with the opening in the sealing element; and
   wherein the actuating device exerts an external force for inwardly displacing the wall of the opening and thereby closing the opening preventing fluid flow therethrough.

2. The attachment according to claim 1, wherein the actuating device and the sealing element are designed for repeated opening and closing of the opening.

3. The attachment according to claim 1, wherein the sealing element includes elastic material.

4. The attachment according to claim 1, wherein the sealing element is made of an elastic material.

5. The attachment according to claim 3, wherein the opening is left open due to the inherent elasticity of the material of the sealing element.

6. The attachment according to claim 1, wherein the actuating device includes an actuating element movable in relation to a base body of the attachment.

7. The attachment according to claim 6, further comprising a locking device interacting with the actuating element in such a way that the actuating element is held in at least one position in a closed way.

8. The attachment according to claim 6, wherein the actuating element is displaceable in the direction of the passage channel of the actuating device.

9. The attachment according to claim 1, wherein the actuating device is movable towards the sealing device to close the opening.

10. The attachment according to claim 1, wherein the sealing device includes a conical sealing region for surrounding a protrusion of the syringe or cartridge.

11. The attachment according to claim 10, in combination with the syringe or cartridge, the conical sealing region surrounding the protrusion.

12. An attachment for a syringe or a cartridge comprising:
    a sealing element having a conical section defining opening for a medium located in the syringe or cartridge or to be introduced into the syringe or cartridge, the conical section having a wall normally in an open position in which the opening is open and inwardly deflectable to a closed position in which the opening is closed; and
    an actuating device defining a conical actuating region for receiving the conical section of the sealing element, the actuating device movable toward the sealing element to move the wall of the conical section from the open position to the closed position;
    wherein the actuating device exerts an external force for inwardly displacing the wall of the opening and thereby closing the opening preventing fluid flow therethrough.

13. The attachment according to claim 12, wherein the sealing device includes a conical sealing region for surrounding a protrusion of the syringe or cartridge.

14. The attachment according to claim 13, in combination with the syringe or cartridge, the conical sealing region surrounding the protrusion.

15. An attachment for a syringe or a cartridge comprising:
    a sealing element having a male conical portion and defining an opening for a medium located in the syringe or cartridge or to be introduced into the syringe or cartridge; and
    an actuating device having a female conical portion for receiving the male conical portion of the sealing element, the actuating device movable toward the sealing element to close the opening;

wherein the actuating device exerts an external force for inwardly displacing a wall of the opening and thereby closing the opening preventing fluid flow therethrough.

16. The attachment according to claim 15, wherein the wall of the opening is normally in an open position in which the opening is open and inwardly deflectable to a closed position in which the opening is closed.

* * * * *